United States Patent
Tew et al.

(10) Patent No.: US 8,431,406 B2
(45) Date of Patent: Apr. 30, 2013

(54) TERPYRIDINE-SUBSTITUTED COMPOUNDS AND RELATED SELECTIVE DETECTION METHODS

(75) Inventors: Gregory N. Tew, Amherst, MA (US); Raja Shunmugam, Amherst, MA (US)

(73) Assignee: University of Massachusetts, Boston, MA (US)

( * ) Notice: Subject to any disclaimer, the term of this patent is extended or adjusted under 35 U.S.C. 154(b) by 704 days.

(21) Appl. No.: 12/229,466

(22) Filed: Aug. 22, 2008

(65) Prior Publication Data

US 2011/0065195 A1    Mar. 17, 2011

Related U.S. Application Data

(60) Provisional application No. 60/965,768, filed on Aug. 22, 2007.

(51) Int. Cl.
*G01N 21/25* (2006.01)
*G01N 33/20* (2006.01)
*G01N 21/64* (2006.01)

(52) U.S. Cl.
USPC ............................. 436/81; 436/74; 436/164

(58) Field of Classification Search ........................ None
See application file for complete search history.

(56) References Cited

U.S. PATENT DOCUMENTS 6,083,758 A * 7/2000 Imperiali et al. ................ 506/12

OTHER PUBLICATIONS

Coronado et al. "Reversible Colorimetric Probes for Mercury Sensing," J. Am. Chem. Soc., 2005, vol. 127 (35), pp. 12351-12356.*
Shunmugam, R; Gabriel GJ; Smith CE; Aamer KA; Tew GN. A Highly Selective Colorimetric Aqueous Sensor for Mercury. Chem. Eur. J. 2008, 14, pp. 3904-3907.
Shunmugam, R; Tew, GN. Unique Emission from Polymer Based Lanthanide Alloys. J. Am. Chem. Soc., 2005, vol. 127, No. 39, 13567-13572.
Shunmugam, R; Tew, GN. Efficient Route to Well-Characterized Homo, Block, and Statistical Polymers Containing Terpyridine in the Side Chain. Journal of Polymer Science: Part A: Polymer Chemistry, vol. 43, 5831-5843 (2005).
Tew, GN; Aamer, KA; Shunmugam, R. Incorporation of terpyridine into the side chain of copolymers to create multi-functional materials. Polymer 46, (2005) 8440-8447.

* cited by examiner

*Primary Examiner* — Shafiqul Haq
*Assistant Examiner* — Galina Yakovleva
(74) *Attorney, Agent, or Firm* — Milstein Zhang & Wu LLC

(57) ABSTRACT

Terpyridine-substituted compounds, compositions and/or related methods, as can be used to selectively detect a wide range of analytes.

9 Claims, 14 Drawing Sheets

Figure 1A
Figure 1B
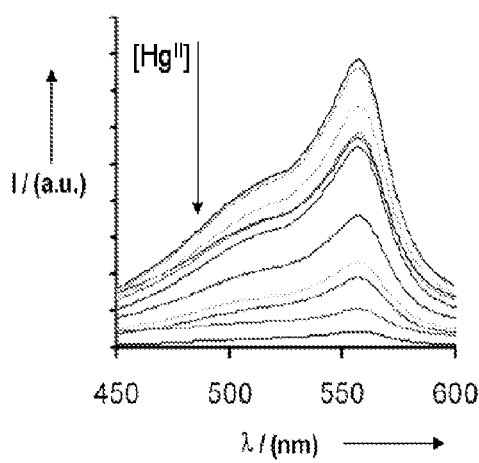
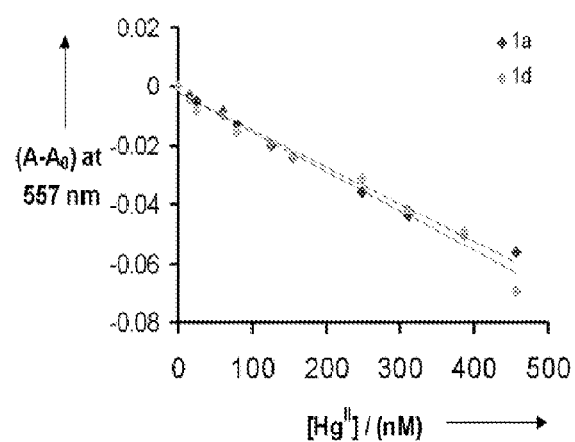

Sarin

Soman

Cyclic Sarin

Soman Surrogate (SOS)

Sarin Surrogate (SAS)

1a-c
1a = H; 1b = O(CH$_2$)$_3$ CH$_3$;
1c = MMA based polymer
Ln = Eu$^{3+}$, Tb$^{3+}$, Dy$^{3-}$

- 1+ Eu3+
- SAS
- SOS
- TBP
- DPP
- TPP
- TEA
- TEP
- PA

TERPYRIDINE-SUBSTITUTED COMPOUNDS AND RELATED SELECTIVE DETECTION METHODS

This application claims priority benefit of application Ser. No. 60/965,768, filed Aug. 22, 2007, the entirety of which is incorporated herein by reference.

The United States government has certain rights to this invention pursuant to support from the Army Research Office pursuant to Grant No. S13100003300000, to the University of Massachusetts.

BACKGROUND OF THE INVENTION

Detection techniques and related methodologies have been and remain active areas of research in a wide range of diverse fields. While selectivity is a primary concern, sensitivity can be equally as important, depending upon the particular end-use application. As common as those issues may be, such detection methods inevitably vary with regard to sensor theory, design and/or operation. An approach to one particular analyte is often unsatisfactory, if effectual at all, with respect to another.

For instance, consider mercury poisoning, a significant threat to human health. In the United States, nearly 87% of mercury emissions result from solid waste incineration and the combustion of fossil fuels. The long atmospheric lifetime of mercury causes contamination across vast quantities of land and water. To make the problem worse, bacteria convert elemental and ionic mercury to methyl mercury adding this potent neurotoxin to the food chain. Mercury poisoning causes serious sensory, motor and cognitive disorders in human beings.

Knowing the seriousness of this problem, significant research efforts have been devoted to improving mercury detection. Current industrial approaches rely on costly, time-consuming methods like atomic absorption/emission spectroscopy or inductively coupled plasma mass spectroscopy, which are not very amenable to portable, convenient "in the field" detection. Therefore, many laboratories have focused on "colorimetric," redox-active, and/or fluorescence chemosensors in the hopes of developing new mercury sensors. Many such sensors are affected by competing metal ions, are incompatible with aqueous media and/or have slow $Hg^{II}$ response times. In all cases, it is critical to selectively detect mercury in the presence of other environmental metals especially $Pb^{II}$ and $Cu^{II}$.

By comparison, a variety of approaches to detect nerve agents have been reported including those based on colorimetric, fluorimetric, gas chromatography and enzymatic assays. A common limitation of these approaches is their general lack of selectivity and/or sensitivity. To make the problem more complex, G-type and V-type agents are organophosphates (OPs); the same chemical class as many widely used pesticides so that detection of the nerve agents typically must complete with a background level of OPs. From a practical sense, colorimetric detection is generally considered simplest since it just requires a color change to be monitored. However, as sensitivity is an issue, fluorescence based sensors can have the potential for wide-range use and application.

As evident from the preceding, a method for mercury detection may not be applicable in or entirely suitable for sensing nerve agents. As a result, the search for a broad-based effective, selective and sensitive molecular approach to a range of detection systems remains an on-going concern in the art.

SUMMARY OF THE INVENTION

In light of the foregoing, it is an object of the present invention to provide a molecular-based approach and/or related methods for analyte detection, overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide a molecular platform adaptable to a variety of detection methodologies, for a diverse range of analytes, without limitation as to analyte medium.

It can also be an object of the present invention to provide such an approach and related methodologies, demonstrating sensitivity and/or selectivity of the sort required for a particular end-use application.

It can also be an object, alone or in conjunction with one or more of the preceding objectives, to promote one or more such methodologies and related systems from the laboratory to practical field, environmental and/or clinical application.

Other objects, features, benefits and advantages of the present invention will be apparent from this summary and the following descriptions of certain embodiments, and will be readily apparent to those skilled in the art having knowledge of various detection techniques and methodologies. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a method of detecting a mercury (2+) species. Such a method can comprise providing a system comprising a compound comprising a terpyridine moiety; contacting such a compound with an analyte medium; and determining the presence of a $Hg^{2+}$ ion in the medium, as can be indicated by a colorimetric or spectrophotometic change in such a system. As illustrated below, such detection can comprise a visible color change of such a system/compound associated with the presence of $Hg^{2+}$ ion. Likewise, representative of various embodiments of this invention, such detection is selective over and in the presence of one or more non-mercury ions or analytes in such a medium. As illustrated below, selective detection can comprise a visible color change distinguishable from contact with other such analytes. In certain such non-limiting embodiments, such a method can be used to detect $Hg^{2+}$ ion, visibly and absent instrumentation (e.g., without spectrophotometric instrumentation), present at a concentration down to about 2 ppm. In certain other non-limiting embodiments, under spectrophotometric conditions and/or analysis, $Hg^{2+}$ ion can be detected at concentrations down to about 2 ppb.

In certain non-limiting embodiments, a terpyridine moiety or a substituted terpyridine moiety can be pendent to a monomeric component of a polymeric compound. In certain such embodiments, without limitation, such a polymeric compound can comprise a poly(alkylene) or poly(alkylene oxide) backbone structure. However, as would be understood by those skilled in the art, such a polymeric compound is limited only by incorporation of or conjugation with terpyridine moieties, using a suitable coupling or linking moiety, sufficient for desired analyte detection, such a polymer or copolymer, or terpyridine or substituted terpyridine moiety thereof, structure limited only by composition, design, desired end-use physical or performance properties sufficient for function in and/or use in conjunction with a system for $Hg^{2+}$ detection. Regardless, in certain non-limiting embodiments, such a polymeric compound can be a statistical copolymer of methylmethacrylate and the terpy-functionalized methyl methacrylamide, of the sort shown below.

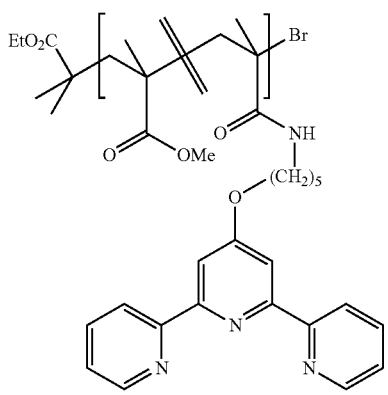

Accordingly, such a system for $Hg^{2+}$ detection can comprise one or more such terpyridine-pendent compounds, polymers or copolymers alone, as part of a medium selected from solid and liquid media and/or in conjunction with a kit. In certain such embodiments, a solid medium can comprise a substrate coupled to such a compound or polymer, such a substrate as can be metallic, polymeric and/or cellulosic. Such a system can be incorporated into an article of manufacture such as a dip stick. In certain such embodiments, such a substrate can comprise a cellulosic component or strip. Contact thereof with a medium comprising one or more analytes can induce colorimetric change, as described above and illustrated below, selectively and in the presence $Hg^{2+}$ ion. As would be understood by those skilled in the art and made aware of this invention, such an analyte medium can be selected from solid, liquid and gaseous media.

In part, the present invention can also be directed to a method of detecting G-type agents and G-type surrogates thereof. Such a method can comprise providing a system comprising a compound comprising a terpyridine moiety complexed to a lanthanide ion, such a complex providing a fluorescence spectrum or a fluorescence intensity at a chosen wavelength; contacting such a terpyridine-lanthanide complex with a medium (e.g., without limitation, a liquid or gaseous medium); and determining the presence of a G-type agent and/or compositional surrogate in the medium, as can be indicated by a change in a fluorescence spectrum or a fluorescence intensity of the terpyridine-lanthanide complex. In certain embodiments, a spectral change can comprise a change in emission intensity. Such a spectral or intensity change can be detected in the presence of a G-type agent and/or a surrogate thereof present at a concentration down to about 75 ppb. Regardless, such detection and/or spectral or intensity change is selective for such agents/surrogates in the presence of non-G-type agents or analytes.

In certain non-limiting embodiments, a terpyridine moiety or a substituted terpyridine moiety can be pendent to a monomeric component of a polymeric compound. In certain such embodiments, without limitation, such a polymeric compound can comprise a poly(alkylene) or poly(alkylene oxide) structure. However, as would be understood by those skilled in the art, such a polymeric compound is limited only by incorporation of or conjugation with terpyridine moieties, using a suitable coupling or linking moiety, sufficient for desired analyte detection, such a polymer or copolymer, or terpyridine or substituted terpyridine moiety thereof, structure limited only by composition, design, desired end-use physical or performance properties sufficient for function in and/or use in conjunction with a system for G-type agent/surrogate detection. Regardless, in certain embodiments, such a polymeric compound can be a poly(methylmethacrylate). While such a compound and a terpyridine moiety thereof can be complexed with a range of available lanthanide ions, good effect can be observed with $Eu^{3+}$, $Tb^{3+}$ and $Dy^{3+}$.

Accordingly, such a system for G-type/surrogate detection can comprise one or more such terpyridine-pendent compounds, polymers or copolymers alone, as part of a medium selected from solid and liquid media and/or in conjunction with a kit. In certain such embodiments, a solid medium can comprise a substrate coupled to such a compound, polymer of copolymer, such a substrate as can be metallic, polymeric and/or cellulosic. Such a system can be incorporated into an article of manufacture, including, but not limited to, a dip stick. In certain such embodiments, such a substrate can comprise a cellulosic component or strip.

In part, this invention can also be directed to a method of using a terpyridine-lanthanide ion complex to detect the presence of a G-type nerve agent. Such a method can comprise providing a compound comprising a terpyridine moiety or a substituted terpyridine moiety or ligand component complexed to a lanthanide ion, such a complex providing a fluorescence spectrum or a fluorescence intensity at a chosen wavelength; contacting such a complex with a liquid or gaseous medium comprising at least one of a G-type agent and a compositional surrogate thereof, such contact for at least one of a time and at agent/surrogate concentration sufficient to affect binding of the lanthanide ion to the terpyridine moiety or ligand component or the substituted terpyridine moiety or ligand component; and detecting a binding effect on such a complex, with the detection comprising a change in the fluorescence spectrum or the flourescence intensity. As discussed above, such detection and/or spectral change can comprise a change in emission intensity, regardless of the presence of one or more non-G-type agents and/or analytes. Without limitation, in certain embodiments, such a terpyridine moiety or a substituted terpyridine moiety can be incorporated in or conjugated with a polymer compound of the sort described herein, such as but not limited to a poly(methylmethacrylate). Regardless of compound design or structure, a complexed lanthanide ion can be selected from, but is not limited to, $Eu^{3+}$, $Tb^{3+}$ and $Dy^{3+}$.

In part, this invention can also be directed to a system comprising such a terpyridine-lanthanide ion complex, such a system, as can comprise a kit, in or on a medium facilitating complex fluorescence and/or change thereof to an extent at least partially sufficient to detect a presence of a G-type agent and/or a compositional surrogate thereof. Accordingly, such a system for G-type/surrogate detection can comprise one or more such terpyridine-pendent compounds, polymers or copolymers alone, as part of a medium selected from solid and liquid media and/or in conjunction with a kit. In certain such embodiments, a solid medium can comprise a substrate coupled to such a compound, polymer of copolymer, such a substrate as can be metallic, polymeric and/or cellulosic.

Such a system can be incorporated into an article of manufacture, including, but not limited to, a dip stick. In certain such embodiments, such a substrate can comprise a cellulosic component or strip.

More generally, but also in conjunction with a terpyridine complex, the present invention can be directed to a method for analyte detection. Such a method can comprise providing a system comprising a compound comprising a terpyridine moiety or a substituted terpyridine moiety complexed to a $Co^{2+}$ or a $Co^{3+}$ ion, such a complex providing a visible spectrum; contacting such a terpyridine complex with an analyte medium (e.g., a liquid, solid or gaseous medium), such contact in the presence of visible light; and determining the presence of an oxidizing agent, such as but not limited to a compound comprising a hydroxy moiety, or a reducing agent, such as but not limited to a compound comprising a chlorohydrocarbon, in such a medium, as can be indicated by a colorimeteric change in the visible spectrum of such a complex. In certain embodiments, as illustrated below, such a complex can comprise $Co^{2+}$ ion, and contact with a compound comprising a hydroxy moiety can change the visible spectrum from a green to a brown. Without limitation, such a hydroxy compound can be selected from saccharides. In certain embodiments thereof, such a sugar can be detected at a concentration less than about 10 μM. In certain other embodiments, such a complex can comprise $Co^{3+}$ ion, and contact with a chlorohydrocarbon compound can change the spectrum of such a complex from a brown to a green—again, such detection with good sensitivity and/or selection in the presence of other analytes.

In certain non-limiting embodiments, such a complexed terpyridine moiety or a substituted terpyridine moiety can be pendent to a monomeric component of a polymeric compound. In certain such embodiments, without limitation, such a polymeric compound can comprise a poly(alkylene) or a poly(alkylene oxide) structure. However, as would be understood by those skilled in the art, such a polymeric compound is limited only by incorporation of or conjugation with terpyridine moieties, using a suitable coupling or linking moiety, sufficient for desired analyte detection. As described above, such a compound, polymer or copolymer, or terpyridine or substituted terpyridine moiety thereof, structure is limited only by composition, design, desired end-use physical or performance properties sufficient for function in and/or use in conjunction with a system for detection of an oxidizing agent (e.g., a hydroxy compound) and/or a reducing agent (e.g., a chlorohydrocarbon compound).

Accordingly, this invention can also be directed to a system comprising a compound comprising a terpyridine moiety complexed to either $Co^{2+}$ or $Co^{3+}$ ion. Such a system can comprised one or more such terpyridine-pendent compounds, polymers or copolymers alone, as part of a medium selected from solid and liquid media and/or in conjunction with a kit. In certain such embodiments, a solid medium can comprise a substrate coupled to such a compound, polymer or copolymer, such a substrate as can be metallic, polymeric and/or cellulosic. Such a system can be incorporated into an article of manufacture including but not limited to a dip stick. In certain such embodiments, such a substrate can comprise a cellulosic component or strip. Contact thereof with a medium comprising one or more analytes can induce a visible color change, as illustrated elsewhere herein. As would be understood by those skilled in the art and made aware of this invention, such an analyte medium can be selected from solid, liquid and gaseous media.

BRIEF DESCRIPTION OF THE DRAWINGS

FIGS. 1A-B. Color change for 1d due to decreasing $Hg^{II}$ concentration. The initial volume of $Hg^{II}$ was 2000 ppm and the final volume was 2 ppm. A) Absorption spectra of 1d in DMSO/water (1:3.5) with decreasing $Hg^{II}$. B) A plot of $(A-A_0)$ vs $Hg^{II}$ concentrations of 1a and 1d.

DETAILED DESCRIPTION OF CERTAIN EMBODIMENTS

Figure 2:
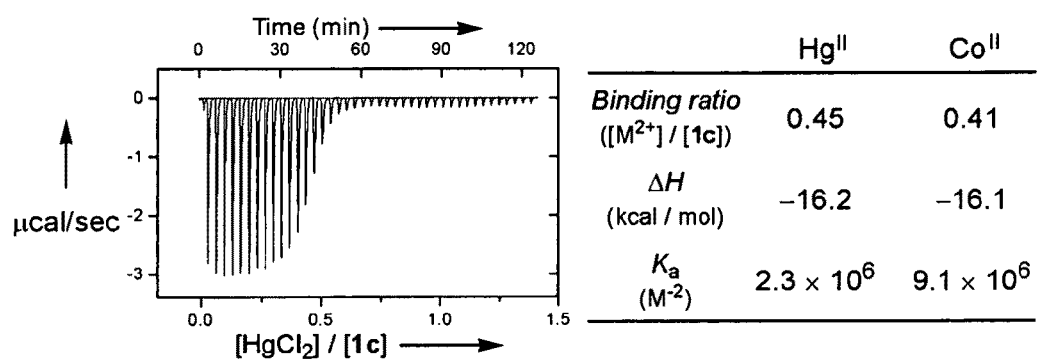
FIG. 2. ITC raw data of the titration of 1c with $Hg^{II}$. [1c]initial=0.15 mM and [$Hg^{II}$]syringe=1.5 mM. Also shown is a table comparing thermodynamic binding parameters of 1c with either $Hg^{II}$ or $Co^{II}$.

As it relates to certain embodiments of this invention, a new colorimetric mercury sensor is directed to binding to a terpy ligand or related compound or polymer (see Scheme 1). Such an approach can be used to selectively detect $Hg^{II}$ ions over a number of environmentally relevant ions including $Ca^{II}$, $Pd^{II}$, $Zn^{II}$, $Cd^{II}$, $Ni^{II}$, $Cu^{II}$, $Fe^{II}$ and others. The response time upon exposure to $Hg^{II}$ is instantaneous. By the "naked eye," the detection limit of $Hg^{II}$ is 2 ppm (25 μM). With a conventional spectrophotometer this detection limit is increased down to 2 ppb (25 nM), which is the current EPA standard for drinking water. Compound 1 appears to be a sensitive and selective colorimetric sensor for $Hg^{II}$, and variations of 1 afford simple yet effective molecular scaffolds for related detection methods.

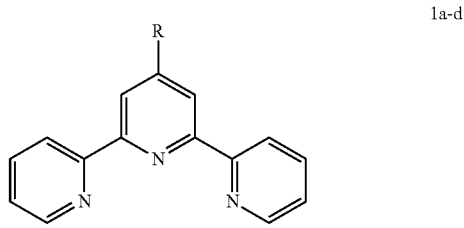

Scheme 1. Terpy derivatives investigated for Hg binding. 1a, R=H; 1b, R=—O(CH$_2$)$_3$—CH$_3$; 1c, R=—(OCH$_2$CH$_2$)$_n$OCH$_3$; 1d, R=MMA based polymer previously reported. The different molecules have no observable differences in the reported experiments except for the 'dip-stick' analysis in which the polymer sample 1d produced more uniform films.

With reference to examples 1-4, below, the selectivity of 1 for $Hg^{II}$ over a number of environmentally relevant metals ions such as $Ca^{II}$, $Ba^{II}$, $Pb^{II}$, $Co^{II}$, $Cd^{II}$, $Ni^{II}$, $Mg^{II}$, $Zn^{II}$ and $Cu^{II}$ was investigated. The addition of $HgCl_2$ in water to a solution of 1 in DMSO/water (1:3.5) caused the immediate appearance of a pink color. Conversely, addition of the other metals to solutions of 1 resulted in little or no color change, except for $Cu^{II}$ which turned slightly blue as expected. The pink color results from binding of $Hg^{II}$ to 1 in the presence of water and the absorption coefficient, ε, of 1b-$Hg^{II}$ is $4 \times 10^4$ Lmole$^{-1}$cm$^{-1}$ at 557 nm. This is for example 13 times larger than the absorption coefficient for 1b-$Co^{II}$ ($0.3 \times 10^3$ Lmole$^{-1}$cm$^{-1}$) at the same wavelength.

In order to understand the influence of excess metal ions on $Hg^{II}$ detection, two different sets of experiments were conducted. In the first experiments, a 10-fold excess of a competing metal ion was added to the solution followed by the addition of $Hg^{II}$. For these experiments, terpy (1) was always in excess so the 10-fold excess is metal ion to $Hg^{II}$ (terpy is 100 fold excess). In all cases, an immediate pink color was observed upon the addition of $Hg^{II}$ without a loss in sensitivity or response time due to the excess terpy present. This confirms the idea that as long as free terpy binding sites are available, $Hg^{II}$ detection can be accomplished rapidly and sensitively regardless of the other ions present. In a second series of experiments, the molar ratio of metal ion was greater than terpy so that $Hg^{II}$ would have to displace the other metal ions for detection to occur. Again a 10-fold excess of metal ion was used (10-fold excess compared to both terpy and $Hg^{II}$). For these experiments, $Ag^I$, $Ba^{II}$, $Pb^{II}$, $Cd^{II}$, $Ca^{II}$, $Mg^{II}$, and $Zn^{II}$ did not limit the ability of terpy to detect $Hg^{II}$. However, $Co^{II}$, $Ni^{II}$ and $Cu^{II}$ did inhibit $Hg^{II}$ detection (see binding constant discussion for $Co^{II}$ below). Despite the influence of $Co^{II}$, $Ni^{II}$ and $Cu^{II}$, it is important to note that $Pd^{II}$ and $Cd^{II}$ did not impact the ability of terpy to detect $Hg^{II}$ since these two ions are routinely cited as important and toxic competitors for molecular based $Hg^{II}$ sensors.

To determine the detection limit, the amount of $Hg^{II}$ added to solutions of 1d was gradually decreased. By 'naked-eye' detection, a lower limit of 2 ppm, or 25 μM, $Hg^{II}$ could be seen. To further quantify the detection limit, a conventional UV-Vis spectrometer was employed to record the changes in the absorption spectra as shown in FIG. 1A. In this manner, the detection limit could be extended down to 2 ppb, or 25 nM, which meets current EPA standards for the maximum allowable level of $Hg^{II}$ in drinking water. The colorimetric response of both 1a and 1d versus the concentration of $Hg^{II}$ is shown to be linear in FIG. 1B. In general, all four structures shown in Scheme 1 detect $Hg^{II}$ with the same detection limit.

In order to gain some insight into the metal chelation between $Hg^{II}$ and 1, isothermal titration calorimetry (ITC) was performed (in triplicate) to evaluate the binding of $Hg^{II}$ and another metal, in this case $Co^{II}$, with terpy (FIG. 2). The good solubility of 1c in 1:3.5 DMSO:$H_2O$ allows metal-terpy association values to be reported in aqueous solutions rather than organic solvents for the first time. Both $Hg^{II}$ and $Co^{II}$ gave the expected binding ratio near 0.5 metal ions per terpy illustrating that even at high metal concentrations, the metal center prefers to have two terpy molecules chelated. In contrast, a $Cu^{II}$/terpy system can be driven to a 1-to-1 binding ratio quite easily. Interestingly, from ITC, it appears that terpy does not have an inherent chelating preference for $Hg^{II}$ over $Co^{II}$ as evidenced by the similar enthalpy and association constants between the two systems (FIG. 2). These results suggest that the selectivity and sensitivity for $Hg^{II}$ depends more strongly on the differences in optical properties than binding strength. They also explain why $Co^{II}$ probably also $Ni^{II}$ and $Cu^{II}$ interferes with $Hg^{II}$ detection.

Nonionic surfactant was added to the system for two reasons: 1) to see if the DMSO concentration could be reduced and 2) to determine if the system was sensitive to amphiphilic impurities. It was determined that only 5% DMSO was needed to make the system completely soluble in water and the colorimeteric 'naked-eye' detection limit reminded unchanged (2 ppb) in presence of surfactant. In addition, chelation experiments with EDTA showed that the response was reversible. Upon addition of two equivalents of EDTA, the pink color disappeared. Then addition of one equivalent of $Hg^{II}$ immediately reproduced the pink signal. This cycle was repeated three times with no observable deviations.

Figure 3:
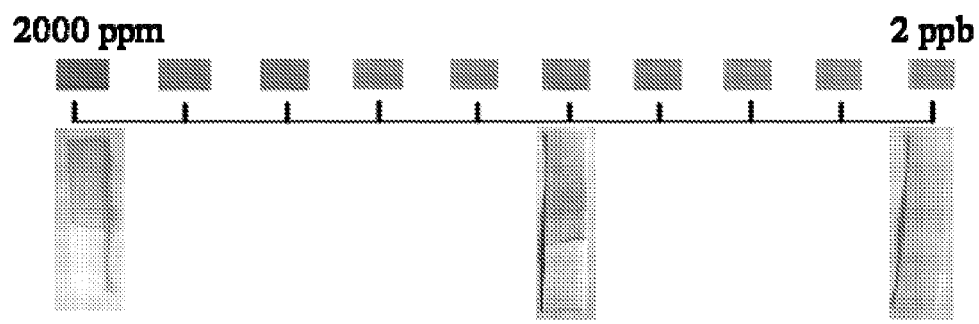
FIG. 3. Demonstration of polymer 1d coated 'dip-sticks' for three different concentrations of $Hg^{II}$.

Motivated by the favorable features of this system in solution, the development of paper strips coated with 1d were investigated to determine the suitability of a 'dip-stick' method for detecting $Hg^{II}$, similar to that commonly used for pH measurements. When the litmus strips coated with 1d were introduced into an aqueous solution of $Hg^{II}$ ions, an immediate color change to pink was observed on contact. Determination of the detection limit for these 'dip-sticks' showed a lower limit of 2 ppb. FIG. 3 shows the 'standard' pink colors for known concentrations of $Hg^{II}$ in solution and three experimental 'dip-sticks.' The litmus paper method could detect $Hg^{II}$ at different pH value ranges from 2.5 to 9 demonstrating that the system works over a wide range of pHs. The development of such a dipstick' approach is extremely attractive for 'in-field' measurements that would not require any additional equipment.

As discussed above, the ability of terpyridine to selectively and sensitively detect $Hg^{II}$ in aqueous environments was demonstrated. A detection limit of 2 ppb, the EPA standard for drinking water, was obtained using either a spectrophotometric or litmus paper method. The response time is instantaneous and the detection limit was achieved even in the presence of excess metal ion competitors of concern as drinking water pollutants. Although $Co^{II}$, $Ni^{II}$, and $Cu^{II}$ do not allow $Hg^{II}$ to displace them, the use of excess terpy easily allows mercury detection in the presence of these ions. In contrast, two typically important competitors for $Hg^{II}$, $Pd^{II}$ and $Cd^{II}$ did not limit terpy's ability to detect $Hg^{II}$. Binding data and absorption spectroscopy for $Hg^{II}$ and $Co^{II}$ suggested the sensitivity arises from the large difference in the absorption coefficient for 1-$Hg^{II}$ complexes. Translation of the solution observations to the litmus paper method could greatly simplify in-field detection of $Hg^{II}$ without the need for special equipment. Despite the simplicity of this system, it has an excellent detection limit and appears to be very versatile.

As can relate to various other embodiments of this invention, terpyridine (terpy)-lanthanide complexes based on compound 1 can also be used as new fluorimetric sensors for G-type agents and compositional surrogates of G-type agents as would be understood by those skilled in the art. (See, e.g., FIG. 4.) The ability to selectively distinguish the G-type surrogate, diethyl chlorophosphate, typically called SAS, from a number of other OPs, including pinacolyl methyl phosphanic acid, typically called SOS is demonstrated. (See, examples 5-11.) Three different lanthanide ions, $Dy^{3+}$, $Tb^{3+}$, and $Eu^{3+}$ were studied along with three derivatives of terpy. Forgiving minor differences in their Stern-Volmer constants ($K_{SV}$), they all showed instantaneous response times and detection levels near 75 ppb, which is below the minimum 1.7 ppm immediately dangerous to life level for sarin and soman set by the Centers for Disease Control and Prevention (CDC).

These materials are luminescent yet at the same time the binding constant between terpy and lanthanide is small compared to the binding of terpy-transition metal complexes, perhaps due to the small bite angle of terpy and the large atomic radii of the lanthanide. Such terpy-lanthanide complexes are acid sensitive and their emission is quenched in the presence of small quantities of acid (e.g. HF or HCl), as produced by the hydrolysis of such G-agents/surrogates—such acid production, as is understood in the art and can be used to designate such a compound as a G-type agent or surrogate thereof Accordingly, such complexes can selectively sense SAS over SOS due, for instance, to the reactive chlorophosphate moiety present in SAS but absent in SOS.

Figure 4:
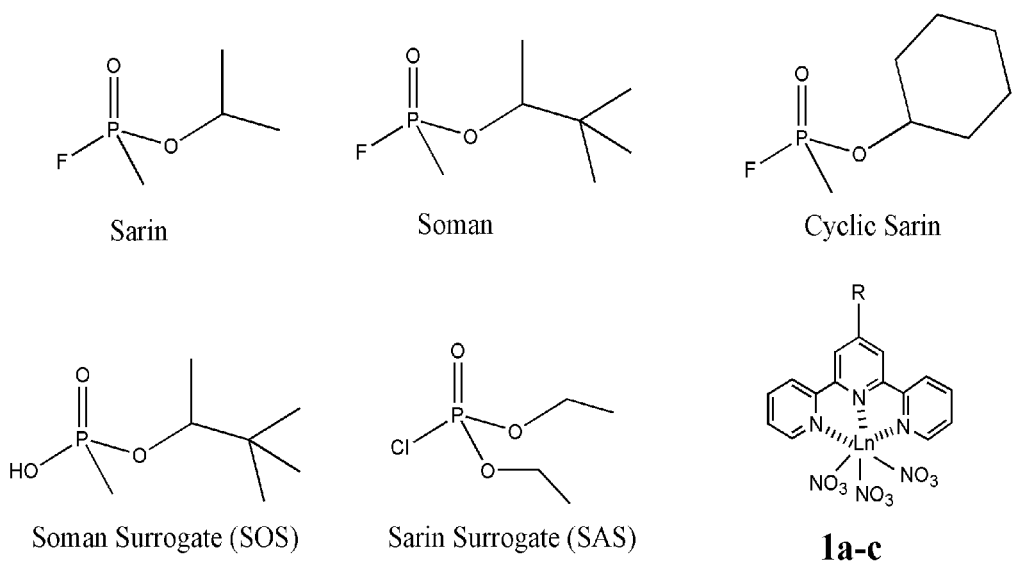
FIG. 4. Chemical structure of sarin, soman and cyclic sarin along with two surrogates, SAS and SOS, and compound 1. SAS, typically called the sarin surrogate, captures the chemical reactivity of the G-type agents while the other, typically referred to as the soman surrogate, SOS, does not. Compounds 1a-c are terpy-lanthanide complexes used for fluorimetric detection. Three emissive lanthanide ions, $Eu^{3+}$, $Tb^{3+}$, $Dy^{3+}$, were studied.
Figure 5:
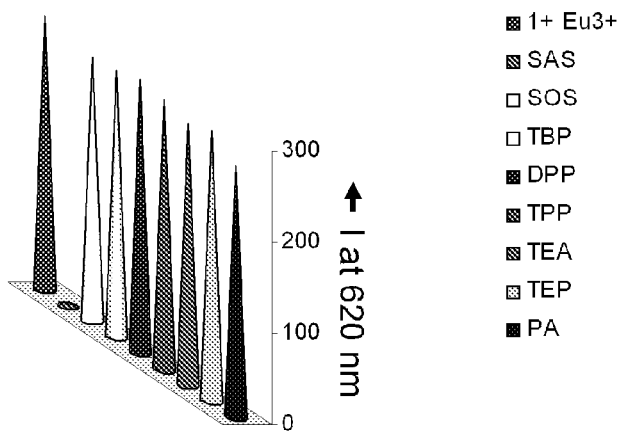
FIG. 5. A plot of emission intensity for 1a-$Eu^{3+}$ (FIG. 4) at 620 nm upon addition of SAS and other OPs, soman surrogate (SOS), tributylphosphate (TBP), diphenylphosphate (DPP), triphenyl phosphine (TPP), triethyl amine (TEA), trietylphosphate (TEP) and phosphoric acid (PA). The concentration of SAS and all other agents was held constant at 75 nM. It is clear that SAS completely quenched the red emission from 1-$Eu^{3+}$ (FIG. 4) while the other agents had little or no change on the emission intensity.
Figure 6A:
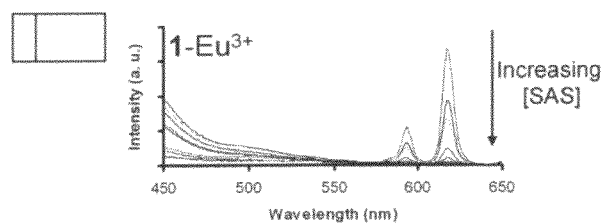
FIGS. 6A-D. Emission spectra of A) 1c-$Eu^{3+}$, B) 1c-$Tb^{3+}$, and C) 1c-$Dy^{3+}$ (FIG. 4) as a function of increasing SAS concentration. The spectra were collected in 1:1 $CHCl_3$:$CH_3OH$ with an excitation wavelength ($E_x$) of 350 nm D) Stern-Volmer plots of SAS $I_o/I$ vs concentration.
Figure 6B:
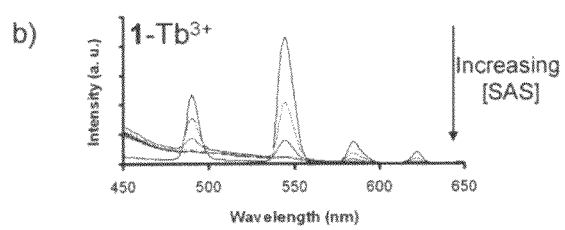
Figure 6C:
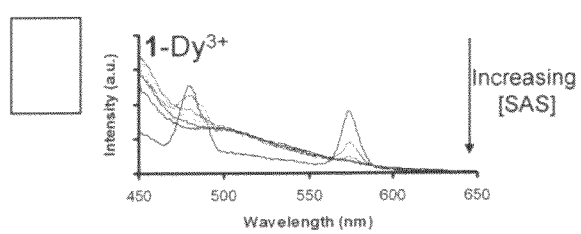
Figure 6D:
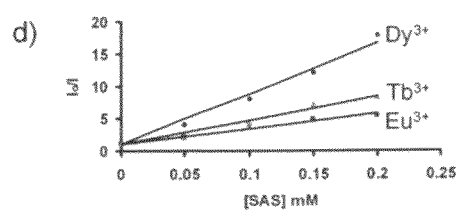

FIG. 5 shows the emission intensity of 1a-$Eu^{3+}$ (FIG. 4) alone and in the presence of SAS, SOS, as well as several other OPs. From this figure, it is clear that only SAS significantly reduces the emission of 1a-$Eu^{3+}$ (FIG. 4) while the other compounds show little or no change in the emission intensity. Very similar results were obtained for 1a-$Dy^{3+}$ and 1a-$Tb^{3+}$ (FIG. 4) as well as terpy-lanthanide complexes based on 1b-c. In addition, the introduction of a 200-fold excess of these OPs to solutions of 1 did not impact the emission or the ability of 1 to detect SAS. In an effort to more quantitatively compare the three lanthanide systems, Stern-Volmer (SV) plots were generated for each system (1c; FIG. 4) from the emission curves shown in FIGS. 6A-C. The SV constant ($K_{sv}$) was obtained as the slope of the line from a plot of fluorescence intensity (Io/I) vs concentration as shown in FIG. 6D. The $K_{SV}$ values were found to be $2.43 \times 10^4$ $M^{-1}$, $3.76 \times 10^4$ $M^{-1}$, $7.82 \times 10^4$ $M^{-1}$ for 1c-$Eu^{3+}$, 1c-$Tb^{3+}$, 1c-$Dy^{3+}$ respectively (FIG. 4). The similarity of the three values suggests they are all quenched equally by SAS, and quenching from solutions of each lanthanide complex was observed under UV-Vis conditions upon introduction of 75 ppb SAS. (See, example 10.)

Figure 7A:
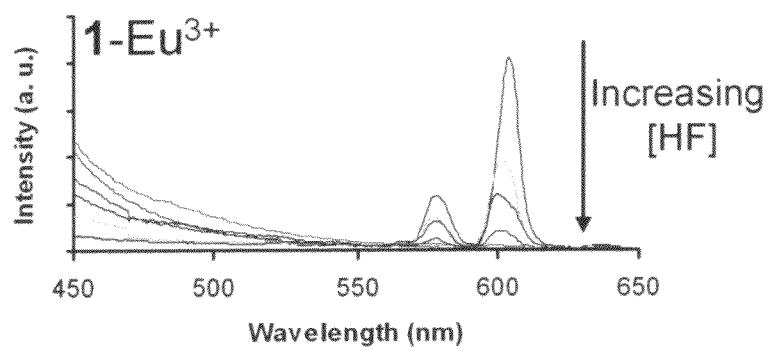
FIGS. 7A-C. Emission spectra of A) 1c-$Eu^{3+}$, B) 1c-$Tb^{3+}$, and C) 1c-$Dy^{3+}$ (FIG. 11) as a function of increasing HF concentration. The spectra was collected in 1:1 $CHCl_3$:$CH_3OH$ with an excitation wavelength ($E_x$) of 350 nm.
Figure 7B:
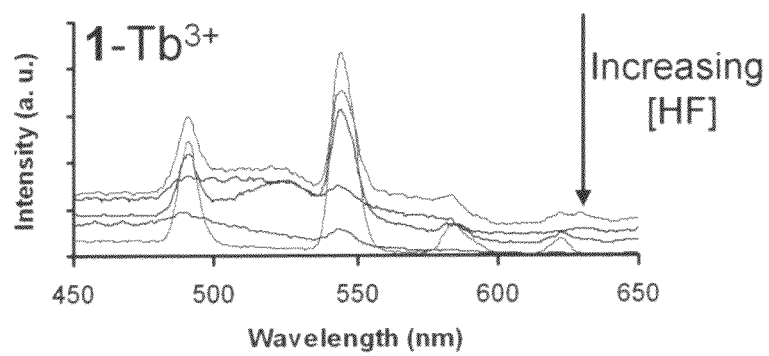
Figure 7C:
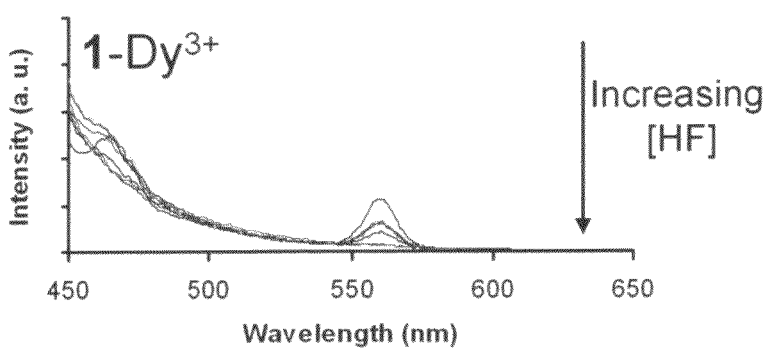
Figure 8A:
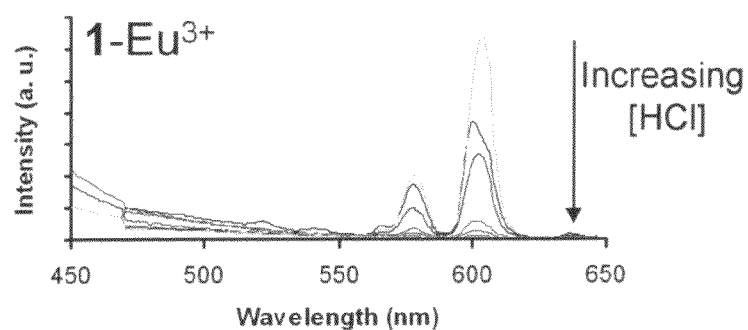
FIGS. 8A-C. Emission spectra of A) 1c-$Eu^{3+}$, B) 1c-$Tb^{3+}$, and C) 1c-$Dy^{3+}$ (FIG. 4) as a function of increasing HCl concentration. The spectra was collected in 1:1 $CHCl_3$:$CH_3OH$ with an excitation wavelength ($E_x$) of 350 nm.
Figure 8B:
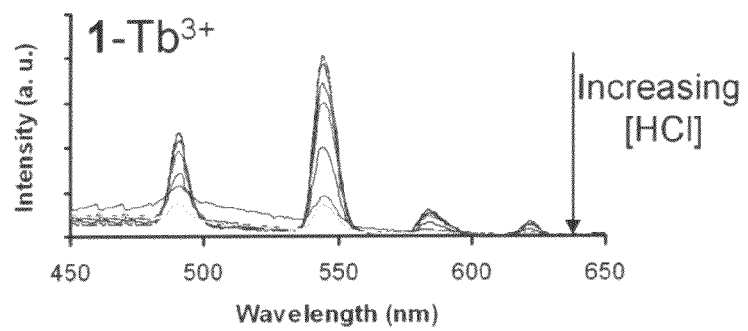
Figure 8C:
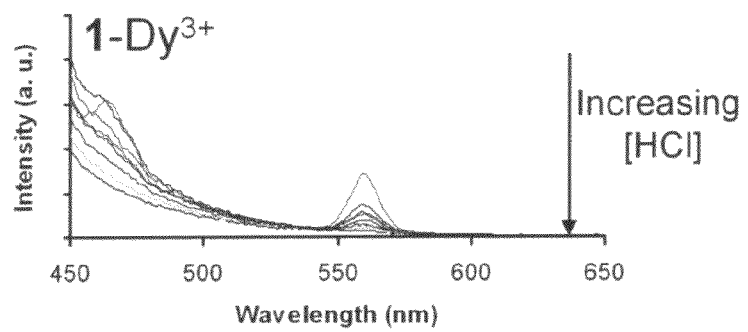
Figure 9A:
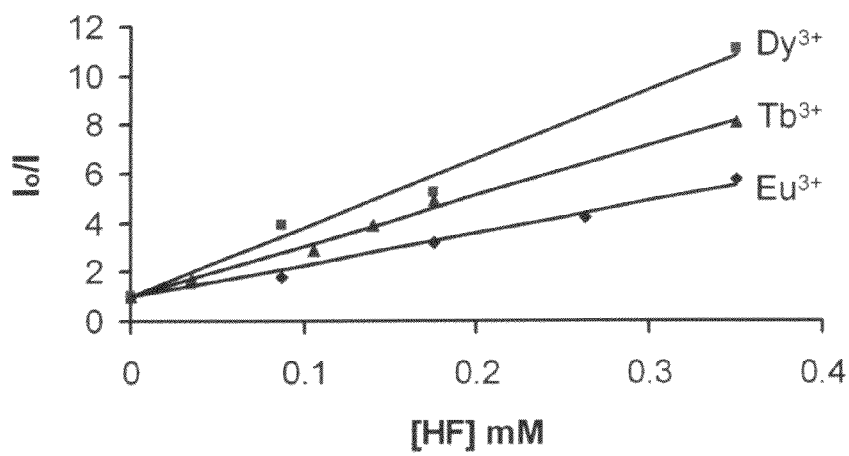
FIGS. 9A-B. Stern-Volmer plots of HF and HCl concentration vs $I_o/I$ from the emission spectra shown in FIGS. 7-8.
Figure 9B:
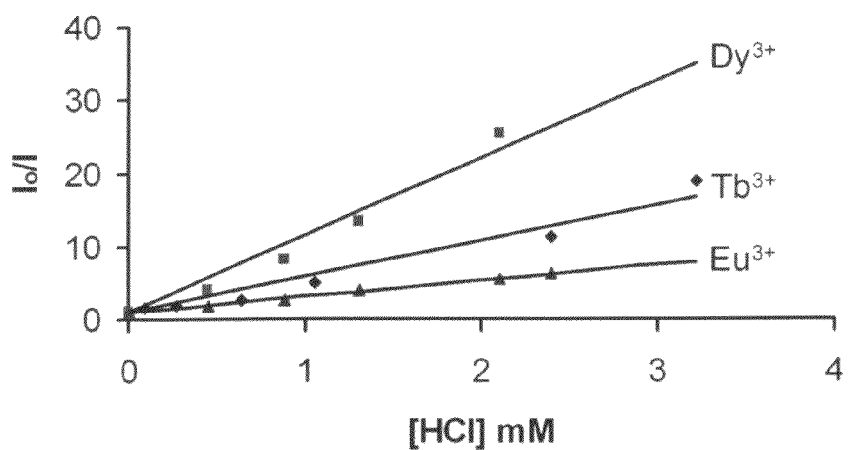
Figure 10:
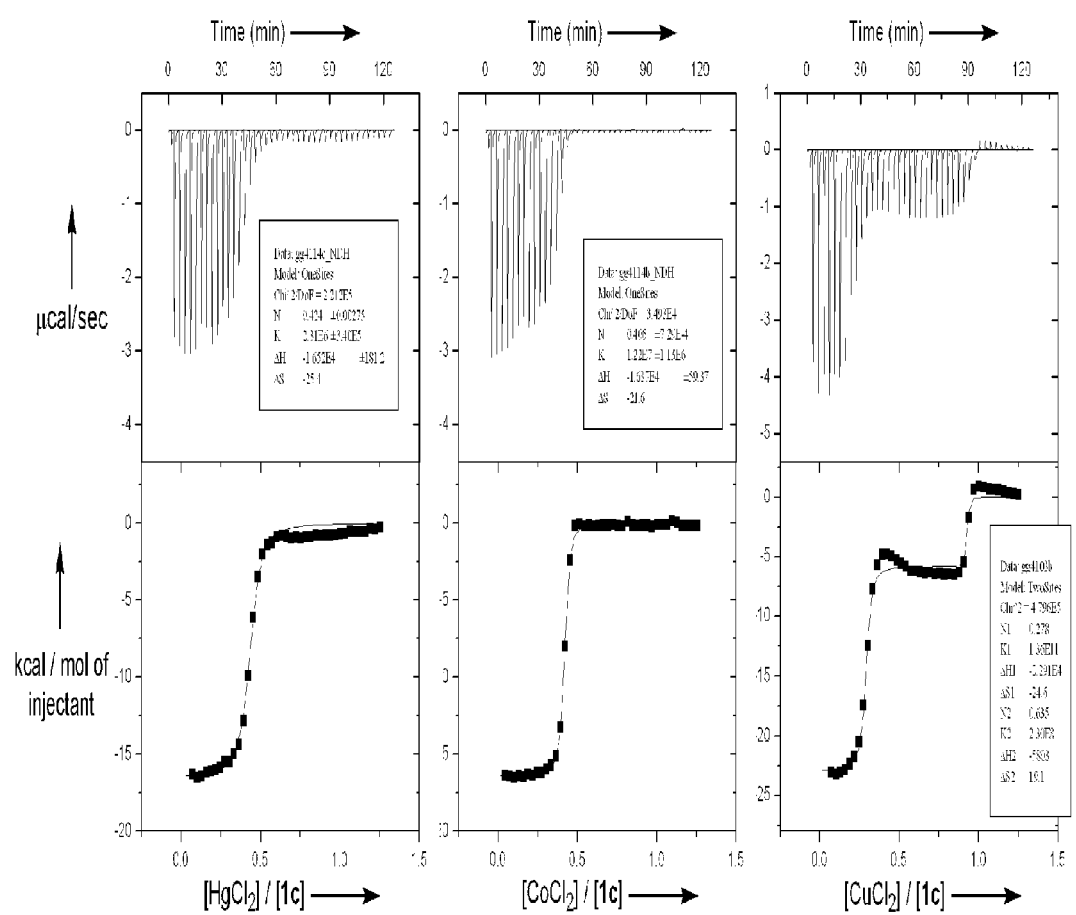
FIG. 10. Representative ITC data. Shown are the raw data (top panels) and integrated heats (bottom panels) of the titration of 1c with different metals ($M^{II}$). [1c]$_{initial}$=0.15 mM and [$M^{II}$]$_{syringe}$=1.5 mM.
Figure 11A:
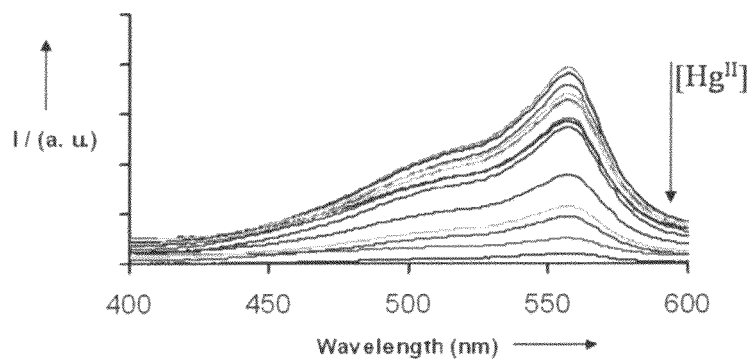
FIGS. 11A-C. Absorption spectra of 1a-c in DMSO/water (1:3.5) with decreasing $Hg^{II}$. Data for 1d is shown in the manuscript.
Figure 11B:
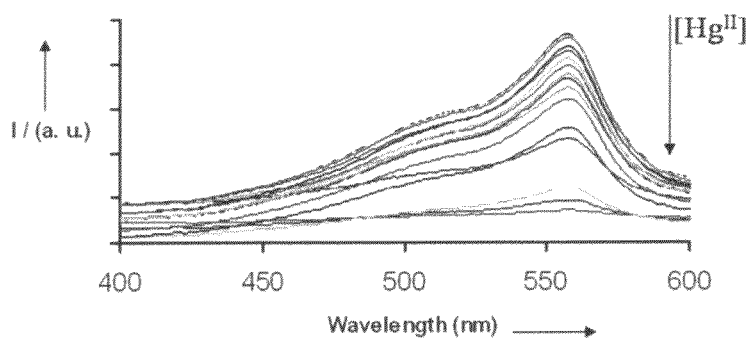
Figure 11C:
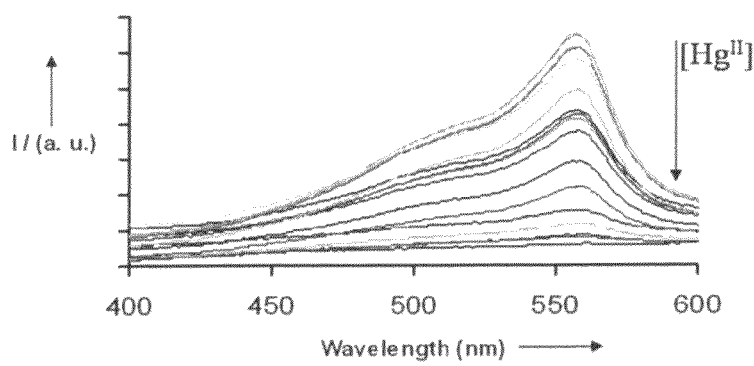
Figure 12:
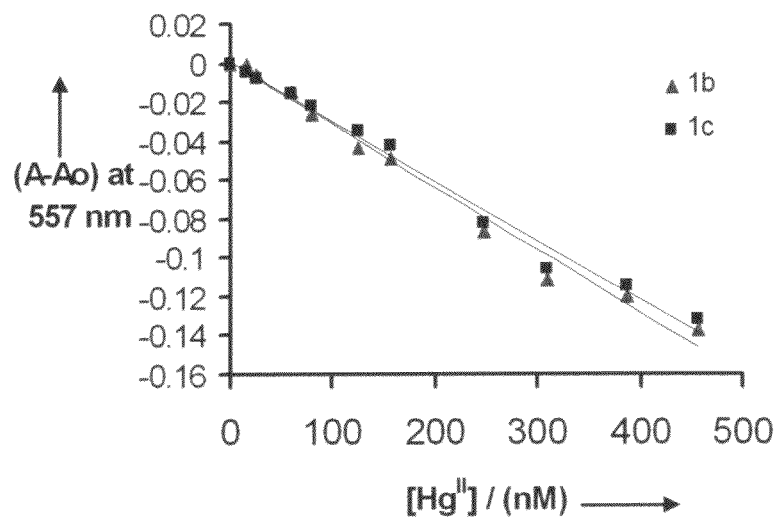
FIG. 12. A plot of $(A-A_0)$ vs $Hg^{II}$ concentrations of 1b and 1c.
Figure 13:
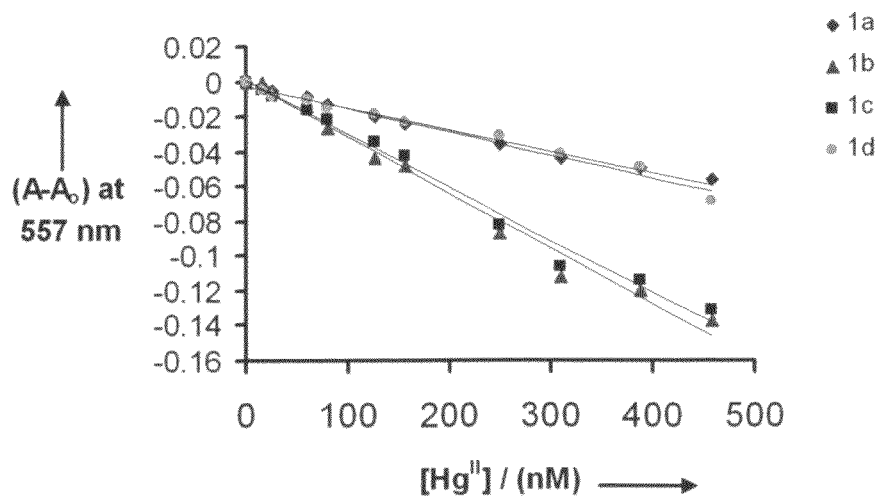
FIG. 13. A plot of $(A-A_0)$ vs $Hg^{II}$ concentrations of 1a-d.
Figure 14A:
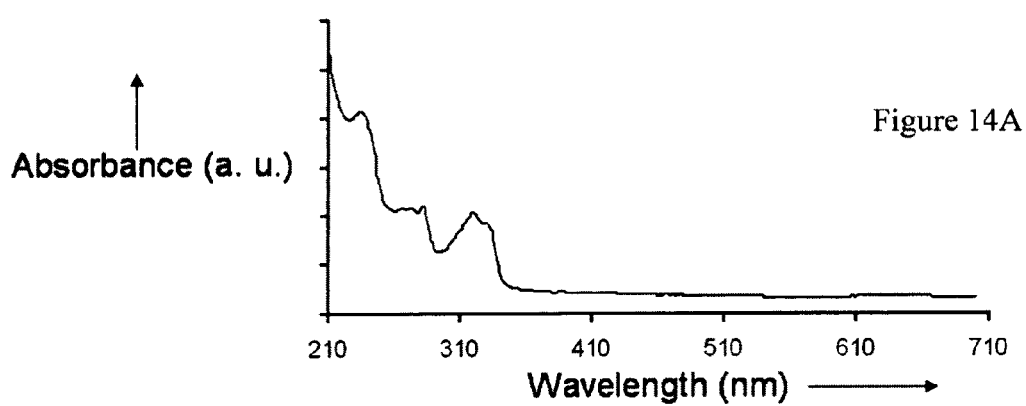
FIGS. 14A-B. Absorption spectra of 1d-$Hg^{II}$ complex A) in acetonitrile; B) in DMSO/water (1:3.5).
Figure 14B:
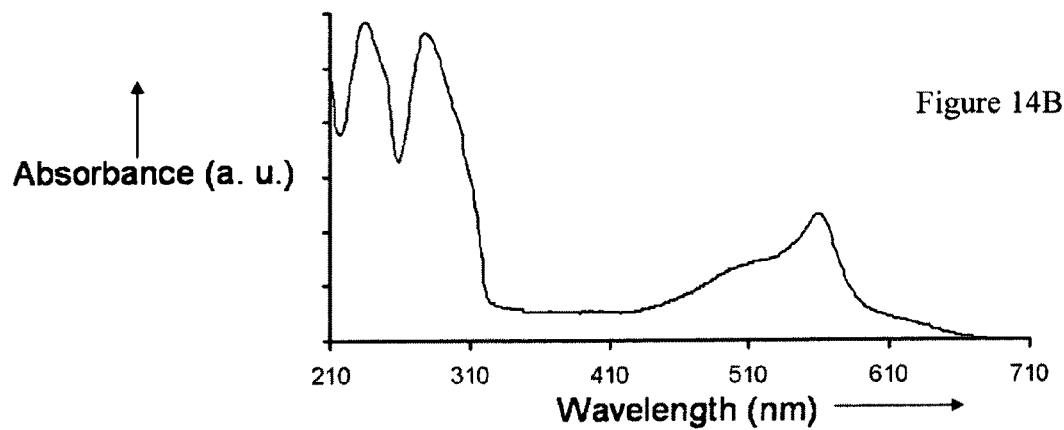

Having demonstrated the sensitivity and selectivity of these terpy-lanthanide complexes for SAS, sensitivity to HCl and HF was considered. HCl is the by-product from hydrolysis of SAS and as a result care was taken in all of the experiments to ensure that residual HCl was not responsible for the loss of emission since HCl quenches the emission of these complexes. Using the $K_{SV}$ as a comparison for quenching efficiency, it was determined for HCl and HF in an identical manner to that described for the data in FIG. 6. The $K_{SV}$ for HCl was measured to be $2.54 \times 10^2$ $M^{-1}$ which is two orders of magnitude less than that for SAS. This means that SAS is much more effective at quenching the emission of these complexes than HCl. NMR studies at much higher concentrations confirmed phosphorylation of the terpy nitrogen implying that the reactivity of SAS as well as the production of HCl from SAS probably contributes to the increased sensitivity observed for SAS. Finally the $K_{SV}$ for HF was measured for two important reasons. First, to ensure that HF quenches these complexes since the real G-warfare agents are fluorophosphates, not chlorophosphates like SAS, and second to compare the $K_{SV}$ of HF with HCl and SAS. The $K_{SV}$ for HF was measured to be $1.29 \times 10^4$ $M^{-1}$. This is similar to SAS and two orders of magnitude higher than HCl. It confirms that HF is about as effective as SAS at quenching the emission of these terpy-lanthanide complexes, yet more effective than HCl. (See, FIGS. 7-9 and Table 3, below.)

As shown above, terpy ligands and related compounds can also provide a simple, yet sensitive and selective, chemical sensor for G-type chemical warfare agents. The system exploits the emission and weak binding of terpy-lanthanide complexes which turn-off in the presence of SAS. The detection limit is 75 ppb, making the system practically useful. The sensitivity for SAS, yet not SOS, indicates that chemical reactivity is an important consideration and one approach to developing selectively sensitive chemical sensors for G-type agents. The $K_{SV}$ for SAS is two orders of magnitude larger than HCl suggesting the added reactivity of SAS increases the detection limit. At the same time, the $K_{SV}$ for HF is similar to SAS indicating these two molecules are similarly effective and that HF is more effective than HCl. If sarin is more reactive than SAS, it would indicate that the detection limit for the real warfare agent is even lower than the 75 ppb measured here for SAS since it would phosphorylate terpy and generate HF.

With reference to examples 12a-d and FIGS. 15-16, below, various other embodiments of this invention can be used for the detection of hydroxy compounds and/or chlorohydrocarbon compounds. As used therewith, various terpyridine-cobalt complexes can be prepared, with cobalt oxidation state used to detect one or another such analytes. If, for instance, $Co^{2+}$ ion is complexed to such a terpyridine compound or moiety, oxidation to $Co^{3+}$, upon exposure to a hydroxy compound, in the presence of light, induces a colorimetric change from green to brown. Conversely, if such a complex comprises $Co^{3+}$ ion, reduction to $Co^{2+}$ upon exposure to a chlorohydrocarbon compound, in the presence of light, induces color change from brown to green. Consistent with various other embodiments of this invention, detection is selective with good sensitivity (e.g., at glucose and other sugar concentrations less than about 10 μM).

EXAMPLES OF THE INVENTION

The following non-limiting examples and data illustrate various aspects and features relating to the compounds, systems, and/or methods of the present invention, including the use of such compounds/systems for selective analyte detection, as described herein. In comparison with the prior art, the present compounds, systems and/or methods provide results and data which are surprising, unexpected and contrary thereto. While the utility of this invention is illustrated through the use of several compounds and analytes which can be detected therewith, it will be understood by those skilled in the art that comparable results are obtainable with various other compounds, systems, methods and/or analytes, as are commensurate with the scope of this invention.

The following and examples 1-4 relate more particularly to selective mercury sensor and detection embodiments of this invention.

Materials. Methyl methacrylate (MMA) was vacuum-distilled and stored in an air free flask in the freezer. 4'-Chloro-2,2':6',2"-terpyridine was purchased from Lancaster and all other chemicals were used as received from Aldrich. Reagent grade DMF was for GPC. All other solvents were used as received. CuBr (98%) was obtained from Fischer Scientifics, PMDETA (99%), ethyl 2-bromoisobutyrate (2- EiBBr, 98%), and anisole (99.7%) were obtained from Aldrich and used without further purification. Mercury (II) chloride was purchased from Acros Organics (Morris Plains, N.J.) and was used as received. Terpyridine amine was synthesized following the procedure as reported earlier. Aamer, K. A.; Tew, G. N., *Macromolecules* 2004, 37, 5, 1990-1993.

Measurements. $^1$H NMR spectra were obtained at 300 MHz with a Bruker DPX-300 NMR spectrometer in $CDCl_3$. The mole percent incorporation of terpyridine into the copolymer was calculated by normalizing the integration values of the $OCH_2$ from the terpyridine functions, and $OCH_3$, from MMA. The copolymer has a 35:65 terpy/MMA ratio. Gel permeation chromatography (GPC) was performed in dimethylformamide (DMF) at room temperature using a PL LC 1120 pump, a Waters R403 differential refractometer, and three PLgel columns (105, 104, and 103 Å) and calibrated with narrow molecular weight poly (methyl methacrylate) standards. UV-vis spectra were obtained using a Perkin-Elmer Lambda 2 series spectrophotometer with PECSS software.

Spectroscopic Materials and Methods. Millipore water was used to prepare all aqueous solutions. Stock solutions of polymer 1 in DMSO and $HgCl_2$ in water were made and diluted to the desired concentration. Titrations of 1 vs $Hg^{II}$ were made by keeping the volume of 1 constant and varying the amount of $Hg^{II}$. Absorption spectra were obtained using a Perkin-Elmer Lambda 2 series spectrophotometer with PECSS software. Samples for absorption and emission measurements were obtained in 1-cm×1-cm quartz cuvettes (3.5-mL volume).

Example 1a

Synthesis of the OSu Monomer. With reference to Scheme 2a, below, a 25 mL round bottom flask was charged with the specified amount of N-hydroxysuccinimide (3.53 g, 30.7 mmole) and triethylamine (4.7 g, 33.7 mmole) in 25 mL THF. The flask was placed in an ice bath at 0° C. followed by the drop wise addition of methylmethacryloyl chloride (MAC) (3 mL, 28.7 mmole) via an additional funnel. The reaction was stirred for 24 h at RT then concentrated under reduced pressure and the excess MAC was removed by dissolving in dichloromethane and washing with DI water, followed by saturated sodium bicarbonate, and finally with water. The pure organic layer was dried over magnesium sulfate, filtered, and evaporated to a solid. The pure monomer was recovered by recrystallization using ethyl acetate-hexane mixture. Yield: 68% $^1$H NMR ($CDCl_3$, ppm): 6.4 (s, H, $H_2C=C$), 5.9 (s, H, $H_2C=C$), 2.87 (s, 4H, OSu H), 2.06 (s, 3H, $CH_3$).

Example 1b

General Procedure for the Homopolymerization of OSu. Tables 1 and 2 summarize experiments performed to optimize the polymerization. In a typical experiment, CuBr (2.4 mg, 0.016 mmol), PMDETA (4.8 mg, 0.024 mmol), and a magnetic stirrer were introduced into a glass vial, which was then sealed with a rubber septum. The vial contents were purged well with nitrogen to remove any dissolved oxygen, and 1 (150 mg, 0.82 mmol) was added and followed by 2-EiBBr (4.3 mg, 0.022 mmol). This vial was then immersed in an oil bath heated at 90° C. The reaction mixture became viscous after a few minutes (typically 10-15 min), at which point the vial was removed from the heat and rapidly cooled. The resulting crude polymeric product was then dissolved by the addition of DMF (1 mL). This solution was slowly added to a stirred solution of acetone (100 mL) to precipitate the polymer as a white solid (0.912 g, 91%). The monomer conversion was calculated from the weight of the polymer recovered after the elimination of the residual monomer under a high vacuum at room temperature.

$M_n$: 12,500. MWD: 1.11 $^1$H NMR ($CDCl_3$, ppm): 2.87 (s, 4H, OSu H), 2.06 (s, 3H, CHs), 1.3 (br s, 2H, $CH_2$). IR (film, $cm^{-1}$): 1808, 1781, 1737, 1682, 1063, 645.

TABLE 1

Conditions and Results for the Copper-Mediated Homopolymerization of an Active Ester Monomer in Anisole

| No. | 1:2-EiBBr:Cu:PMDETA | Temperature (° C.) | Time (min) | Yield (%) | $M_n$ Calculated | $M_n$ Observed | Polydispersity Index |
|---|---|---|---|---|---|---|---|
| 1 | 100:1:1:2 | 90 | 30 | 72 | 18,300 | 15,800 | 1.26 |
| 2 | 50:1:1:2 | 90 | 15 | 89 | 9,150 | 12,300 | 1.10 |
| 3 | 40:1:1:2 | 90 | 10 | 76 | 7,320 | 8,500 | 1.12 |
| 4 | 25:1:1:2 | 90 | 5 | 80 | 4,575 | 8,300 | 1.16 |
| 5 | 10:4:1:2 | 30 | 10 h | 50 | 1,830 | 8,100 | 1.16 |
| 6 | 50:1:1:1[a] | 90 | 48 h | — | 9,150 | — | — |

[a]Bipyridyl was used instead of PMDETA, and no polymerization was observed.

Example 1c

Impact of the Reaction Concentration on the Polymerization. The overall concentration of the reaction was found to be critical for the outcome of the polymerization. When the polymerization was carried out above 75 wt % solvent, no polymerization occurred. At 60 wt % solvent, a yield of 60% was obtained, whereas the maximum yield of 91% was generated at 50 wt % solvent. In these last two cases, the MWD remained well controlled. It was also determined that these polymerizations could be performed at room temperature, generating polymers with narrow MWDs and reasonable MWs, although it appears that the initiation efficiency of 2-EiBBr was reduced because the observed $M_n$ was four times larger than the calculated value.

Example 2a

Procedure for the Copolymerization of OSu. In a typical experiment, a dry vial equipped with a stir bar was charged with CuBr (4.3 mg, 0.033 mmole) under a flowing stream of nitrogen. To this, specified amounts of PMDETA (8.5 mg, 0.049 mmole) and anisole (0.3 mL) were added. After this, MMA (85 mg, 0.82 mmole) and Osu (150 mg, 0.819 mmole) were added. The reaction mixture was purged well with the stream of nitrogen to remove the dissolved oxygen. Finally, copolymerization was carried out by immersing the reaction vial in an oil bath maintained at 90° C. After 10 mins the reaction mixture was cooled and then the crude polymeric product was dissolved by the addition of DMF (1 mL). This solution was slowly added to a stirred solution of methanol-water mixture (60:40) to precipitate the polymer as a white solid (69%). Mn=11,250; PDI=1.21 $^1$H NMR (CDCl$_3$, ppm): 3.6 (OCH$_3$), 2.87 (s, 4H, OSu H), 2.06 (s, 3H, CH$_3$), 1.3 (s, 2H, CH$_2$) IR (Film, cm$^{-1}$): 1808, 1781, 1741, 1682, 1063, 645.

Example 2b

General Procedure for the Copolymerization of OSu. Table 2 summarizes the experimental conditions, MWs, and MWDs for statistical copolymers.

TABLE 2

Conditions and Results for the Ni- and Ru-Mediated Homopolymerization of an Active Ester Monomer in Anisole

| No. | OSu:2-EiBBr:Al:Ni | Temperature (° C.) | Time (h) | Yield (%) | $M_n$(Observed) | Polydispersity Index |
|---|---|---|---|---|---|---|
| 1 | 15:1:0:1 | 90 | 13 | 20 | 725 | 1.01 |
| 2 | 15:1:1:1 | 90 | 1.5 | 50 | 27,900 | 1.58 |
| 3 | 15:1:2:1 | 90 | 1.5 | 40 | 18,500 | 1.54 |
| 4 | 15:1:3:1 | 90 | 1.5 | 60 | 20,000 | 1.48 |
| 5 | 15:1:5:1 | 90 | 1.5 | 66 | 21,000 | 1.45 |
| 6 | 15:1:10:1 | 90 | 1.5 | 87 | 12,300 | 1.26 |
| 8[a] | 15:1:0:1 | 90 | 13 | — | — | — |
| 9[a] | 15:1:1:1 | 90 | 1 | 45 | 21,400 | 1.52 |
| 10[a] | 15:1:2:1 | 90 | 1 | 70 | 26,700 | 1.72 |
| 11[b] | 50:1:0:0 | 90 | 6 h | 50 | 23,000 | 1.40 |

[a]The Ru catalyst was used instead of Ni, and no control in polymerization was observed.
[b]The polymerization was carried out in the absence of catalyst and ligand systems.

Example 2c

Note about Monomer Consumption in the Statistical Copolymerization. In a typical experiment, four dry vials equipped with a stirring bar were charged with CuBr (4.3 mg, 0.033 mmol), PMDETA (8.5 mg, 0.049 mmol), and anisole (0.6 mL) under a flowing stream of nitrogen. After this, MMA (85 mg, 0.82 mmol) and 1 (150 mg, 0.819 mmol) were added. Finally, copolymerization was carried out by the immersion of the reaction vial in an oil bath maintained at 90° C. The polymerization was stopped at regular intervals (5, 10, 15, and 20 min). The reaction mixtures were cooled, and then the crude polymeric product was dissolved by the addition of DMF. SEC and NMR were collected to monitor the MW, MWD, yield, and monomer conversion. Preliminary experiments were conducted to check the randomness of the copolymer. A series of polymerizations were started and terminated prematurely so that the copolymer content could be monitored as a function of time. The polymerizations with comonomer ratios of 60:40 1 to MMA and a target MW of 8000 were initiated by the usual method of heating in a 90° C. oil bath, but they were terminated at time intervals of 5, 10, 15, and 20 min. 1H NMR, SEC, and the total yield were determined for the four samples. The MW increased from 3000 to 6500, whereas the monomer composition was determined to be 90:10, 72:28, 61:39, and 61:39 for the four time intervals, respectively. The yield increased from 52 to 81% over the course of the reaction. NMR confirmed the presence of unreacted 1 throughout the polymerization. These experiments support the copolymerization of the two monomers.

Example 2d

Preparation of the Polystyrene [Poly(S)] Macroinitiator. As can be used to illustrate other copolymers of this invention, a Schlenk tube equipped with a 24/40 ground glass joint opening and a sidearm with a two-way stopcock (for gas flow regulation) was used in all the polymerizations. After the addition of CuBr (2.5 g, 17.42 mmol) under a stream of dry nitrogen gas, the opening of the Schlenk tube was sealed, and the tube was evacuated and backfilled with nitrogen three times. Deoxygenated S (40 mL, 350 mmol) and PMDETA (3.0 g, 17.3 mmol) were added via gastight syringes. The mixture was stirred until a homogeneous solution of light green color was obtained. After this, 2-EiBBr (3.5 g, 17.9 mmol) was added to the flask under a stream of nitrogen. This mixture was carefully degassed through several freeze-thaw cycles to remove any dissolved oxygen, and the polymerization was carried out at 90° C. in an oil bath maintained at this temperature for 2 h.

$M_n$: 3000. MWD: 1.07. $^1$H NMR (CDCl$_3$, ppm): 7.26, 6.90 (m, Ar—H), 1.25 (s, CH$_2$). IR (film, cm$^{-1}$): 2928, 1600, 700.

Example 2e

General Procedure for the Block Copolymerization Synthesis. For purpose of illustration, demonstrating other copolymer availability, a known quantity of previously synthesized and purified poly(S) macroinitiator (110 mg, 0.601 mmol) was dissolved in anisole (0.5 mL). The specified volume of this solution (0.5 mL) was introduced to the glass vial, which contained CuBr (9.1 mg, 0.063 mmol), PMDETA (20 mg, 0.12 mmol), and 1 (400 mg, 2.2 mmol) under a nitrogen flow. After being stirred to generate homogeneous solutions, the reaction mixture was placed in an oil bath at 90° C. After polymerization, typically 2 h, the resulting crude polymeric product was dissolved by the addition of DMF (1 mL). This solution was slowly added to a stirred solution of an McOH/water mixture (60:40) to precipitate the polymer as a white solid (71%). The conversion was calculated by the weighing of the polymer after precipitation and thorough drying.

Reference is made to Scheme 2b illustrating various other copolymers useful in conjunction with this invention. Such copolymers can be used as described elsewhere herein for $Hg^{2+}$, G-type agent/surrogate, hydroxy compound and/or chlorohydrocarbon detection.

Example 3

Procedure for Post Polymer Modification to Attach Terpy. A 2 mL vial was charged with random copolymer of (60 mg, 0.21 mmole), amine functionalized terpy, (120 mg, 0.32 mmole) and a magnetic stirring bar. The vial was sealed with a septum and purged with nitrogen. Anhydrous DMSO (0.3 mL) was injected and the reaction mixture stirred until it became homogeneous. TEA (25 µL, 0.24 mmole) was then added under nitrogen and the vial was placed in an oil bath at 60° C. for 3 h. The polymeric product was isolated by precipitation with acetone. Yield: 96% $^1$H NMR (CDCl$_3$, ppm): 8.69 (br, 2H, pyridine H), 8.62 (br, 2H, pyridine H), 8.00 (br, 2H, pyridine H), 7.85 (br, 2H, pyridine), 7.32 (br, 2H, pyridine H), 7.26, 6.90 (m, Ar—H), 4.15 (br, 2H, OCH$_2$), 3.95 (br, 2H, OCH$_2$), 3.60 (br, 3H, OCH$_3$), 1.95 (s, 2H, CH$_2$), 1.84 (br, 2H, CH$_2$), 1.50 (br, 4H, CH$_2$), 1.33 (br, 6H, CH$_2$), 1.00-0.88 (br, 3H, CH$_3$). IR (Film, cm$^{-1}$): 1726, 1643, 1583, 1447, 1357, 1197.

Scheme 2a. Synthesis of copolymers of OSu and MMA via Cu/PMDETA-catalyzed ATRP followed by synthetic conversion of the active esters to incorporate terpy pendent groups.

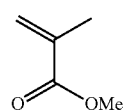

+

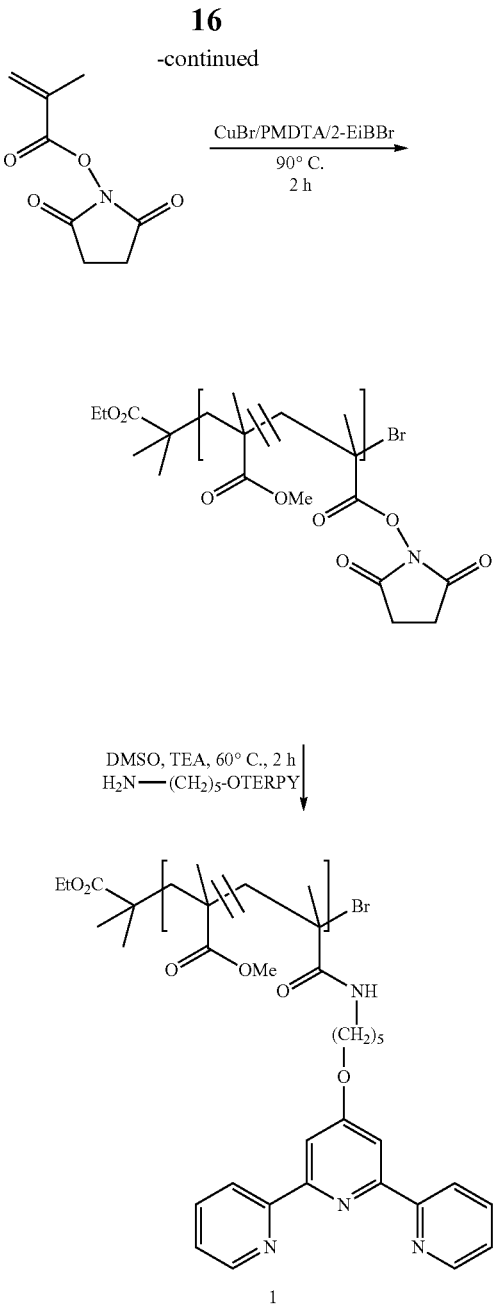

Scheme 2b. Synthesis of various copolymers of 1 and other vinyl monomers including MMA, nBMA, PEGMA, and Styrene.

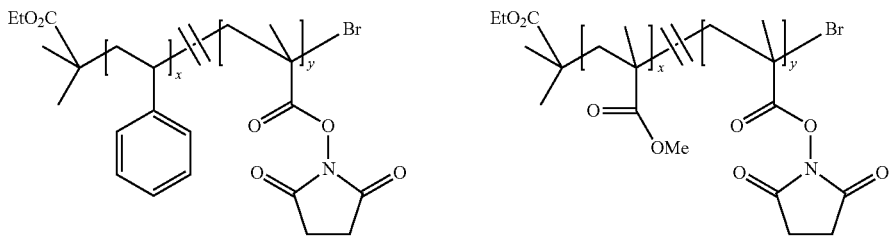

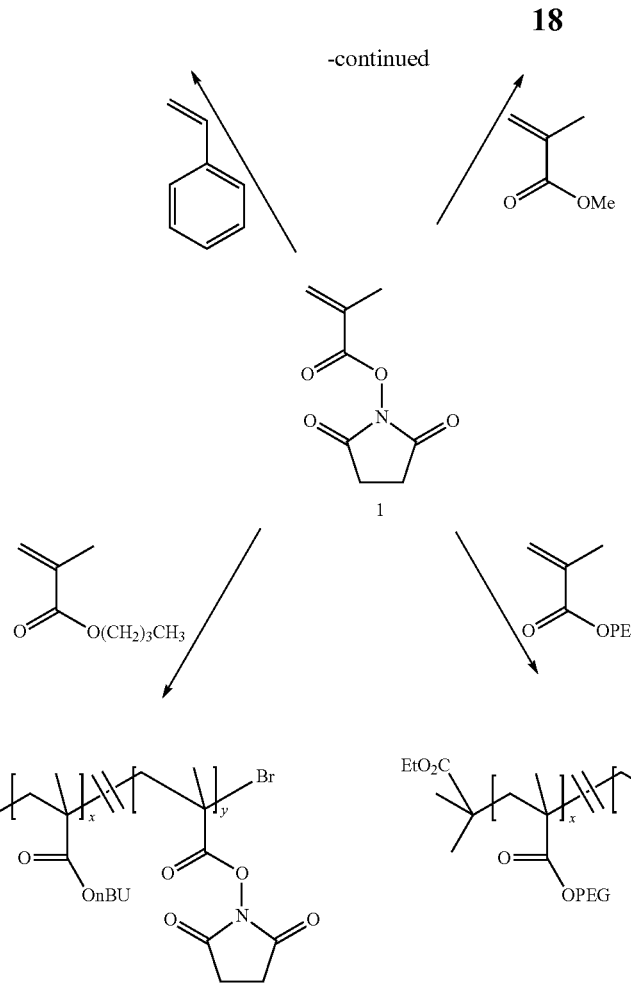

Example 4

Procedure for ITC Experiments. Experiments were performed on a VP-ITC microcalorimeter from Microcal Inc. (Northampton, Mass.) and followed the experimental setups detailed in literature. Brandts, J. F.; Wiseman, T.; Williston, S. *Anal. Biochem.* 1989, 179. All solutions were made in 1:3.5 DMSO:MilliQ water that had been previously degassed for 20 min by sonication. For a typical ITC run the instrument chamber contained a solution of 1c (0.15 mM) while a 1.5 mM solution of metal (diclhoride salt) was taken up in the 250 μL injection syringe. The syringe was assembled into the chamber for equilibration while stirring at 300 rpm. The baseline heat signal (set at 10 μcal/sec) and chamber temperature (set at 30° C.) usually stabilized within 20 minutes before a first injection of 2 μL was performed. (This first data point was not included in the analysis as recommended by Microcal Inc.) The next 41 injections (enough to be reach saturation) were 4 μL each added over 8 sec and spaced 3 minutes apart. ITC runs of metal added to solvent, and solvent added to 1c were also performed and gave negligible heats. ORIGIN software provided by Microcal Inc. gave excellent data fitting results from which association constants, enthalpy, and binding stoichiometry could be obtained. Experiments were performed in triplicate on different days with freshly made solutions. See, FIGS. 10-14.

The following and examples 5-11 relate more particularly to selective G-type agent/surrogate detection and related embodiments of the invention.

Materials. The polymer was previously reported but listed here for easier access. (See, Shunmugam, R.; Tew, G. N. *J. Polym. Sci., Part A: Polym. Chem.* 2005, 43, (23), 5831-5843.) Methyl methacrylate (MMA) was vacuum-distilled and stored in an air free flask in the freezer. 4'-Chloro-2, 2':6',2''-terpyridine was purchased from Lancaster and all other chemicals were used as received from Aldrich. Reagent grade DMF was for GPC. All other solvents were used as received. CuBr (98%) was obtained from Fischer Scientifics, PMDETA (99%), ethyl 2-bromoisobutyrate (2-EiBBr, 98%), and anisole (99.7%) were obtained from Aldrich and used without further purification. Terpyridine amine (1) was synthesized following the procedure as reported earlier. (See, Aamer, K. A.; Tew, G. N. *Macromolecules* 2004, 37, (5), 1990-1993.)

Diethyl chlorophosphate (SAS) and pinacolyl methyl phosphonic acid (SOS) were purchased from Aldrich. Before each experiment, SAS was passed through basic alumina to remove any residual HCl and the pH of the solution also measured regularly.

Measurements. UV-vis spectra were obtained using a Perkin-Elmer Lambda 2 series spectrophotometer with PECSS software. Fluorescence spectra were obtained using a Perkin-Elmer LS 55 luminescence spectrometer with an excitation wavelength of 350 nm. IR spectra were obtained using a Bio-Rad FTS 3000 Excalibur Series. The pictures of lanthanide emission were taken using a handheld UV long wavelength lamp.

Example 5

General Procedure for Copolymerization of OSu. In a typical experiment, a dry vial equipped with a stir bar was charged with CuBr (4.3 mg, 0.033 mmole) under a flowing stream of nitrogen. To this, specified amounts of PMDETA (8.5 mg, 0.049 mmole) and anisole (0.3 mL) were added. After this, MMA (85 mg, 0.82 mmole) and the OSu monomer (150 mg, 0.819 mmole) were added. The reaction mixture was purged well with the stream of nitrogen to remove the dissolved oxygen. Finally, copolymerization was carried out by immersing the reaction vial in an oil bath maintained at 90° C. After 10 mins the reaction mixture was cooled and then the crude polymeric product was dissolved by the addition of DMF (1 mL). This solution was slowly added to a stirred solution of methanol-water mixture (60:40) to precipitate the polymer as a white solid (69%). Mn=11,250; MWD=1.21 $^1$H NMR (CDCl$_3$, ppm): 3.6 (OCH$_3$), 2.87 (s, 4H, OSu H), 2.06 (s, 3H, CH$_3$), 1.3 (s, 2H, CH$_2$) IR (Film, cm$^{-1}$): 1808, 1781, 1741, 1682, 1063, 645.

Example 6

Procedure for Post Polymer Modification to Attach Terpy. A 2 mL vial was charged with the random copolymer (Table 1, entry 2) whose molar ratio was 35:65 OSu:MMA (60 mg, 0.21 mmole), amine functionalized terpy, 1, (120 mg, 0.32 mmole) and a magnetic stirring bar. The vial was sealed with a septum and purged with nitrogen. Anhydrous DMSO (0.3 mL) was injected and the reaction mixture stirred until it became homogeneous. TEA (25 µL, 0.24 mmole) was then added under nitrogen and the vial was placed in an oil bath at 60° C. for 3 h. The polymeric product, 2, was isolated by precipitation with acetone. Yield: 96% $^1$H NMR (CDCl$_3$, ppm): 8.69 (br, 2H, pyridine H), 8.62 (br, 2H, pyridine H), 8.00 (br, 2H, pyridine H), 7.85 (br, 2H, pyridine), 7.32 (br, 2H, pyridine H), 4.15 (br, 2H, OCH$_2$), 3.95 (br, 2H, OCH$_2$), 3.60 (br, 3H, OCH$_3$), 1.95 (s, 2H, CH$_2$), 1.84 (br, 2H, CH$_2$), 1.50 (br, 4H, CH$_2$), 1.33 (br, 6H, CH$_2$), 1.00-0.88 (br, 3H, CH$_3$). IR (Film, cm$^{-1}$): 1726, 1643, 1583, 1447, 1357, 1197. The IR does not show any bands at higher wavenumber that might be associated with carboxylate groups produced by hydrolysis of the active ester.

Example 7

Procedures for Lanthanide Metal Incorporation. All solutions were prepared so that the molar ratio of terpy units to metal ion was known. In a typical experiment, independent solutions of Europium (III) nitrate, Terbium (III) nitrate, Dysprosium (III) nitrate (typically 0.012 mM), and molecule 1 (0.15 mM) were first prepared in a MeOH—CHCl$_3$ (1:1) mixture. Then aliquots of each solution were mixed to the appropriate molar ratios.

Example 8

Stern-Volmer Experiments. For the $K_{SV}$ measurements reported, aliquots of the 5 wt % HF and HCl in water and SAS in CHCl$_3$ solutions were added respectively for the quenching of lanthanide emission and spectra recorded for the SV constant calculations. For 1-Eu$^{3+}$ (FIG. 4), the quenching intensity at 620 nm was used to calculate the $K_{sv}$. For 1-Tb$^{3+}$ (FIG. 4), the quenching intensity at 543 nm was used while for 1-Dy$^{3+}$ (FIG. 4), the quenching intensity at 580 nm was used to calculate the $K_{sv}$.

TABLE 3

| $K_{SV}$ values (in M$^{-1}$) for SAS, HF and HCl quenching. | | | |
|---|---|---|---|
| Sample | SAS | HF | HCl |
| 1-Eu$^{3+}$ | 2.43 × 10$^4$ | 1.29 × 10$^4$ | 2.54 × 10$^2$ |
| 1-Tb$^{3+}$ | 3.76 × 10$^4$ | 2.09 × 10$^4$ | 4.91 × 10$^2$ |
| 1-DY$^{3+}$ | 7.82 × 10$^4$ | 2.77 × 10$^4$ | 1.05 × 10$^3$ |

Example 9

Emission Experiments. Emission spectra (FIGS. 6-8) for all solutions were measured with an excitation wavelength of 350 nm. The solutions were diluted to an OD between 0.05-0.02 at 350 nm. Typically the slit widths were 2.5 mm and the scan rate was 200 nm/min. Slit widths and scan rates were adjusted to allow adequate intensity, if needed.

Example 10

UV-Vis experiments. The absorption spectra for all solutions were measured in a quartz cell at concentrations so that the total absorbance was less than 1 abs. units.

Example 11

Model Compounds. Lanthanide ion incorporation into the model compounds followed similar procedures as reported above for the polymer solutions. Separate equal molar concentration solutions of Europium (III) nitrate, Dysprosium (III) nitrate, Terbium (III) nitrate, 1a and 1b (FIG. 4) were prepared in 1:1 MeOH—CHCl$_3$. Then aliquots of these solutions were mixed and allowed to stir for 10 mins. Emission experiments were performed in solution as described above.

Example 12a

With reference to the synthetic procedures of examples 1-3, various compounds and polymers with pendent terpyridine moieties can be prepared and complexed with either Co$^{2+}$ or Co$^{3+}$ ion, in a manner analogous to that described in example 7.

Example 12b

Figure 15A:
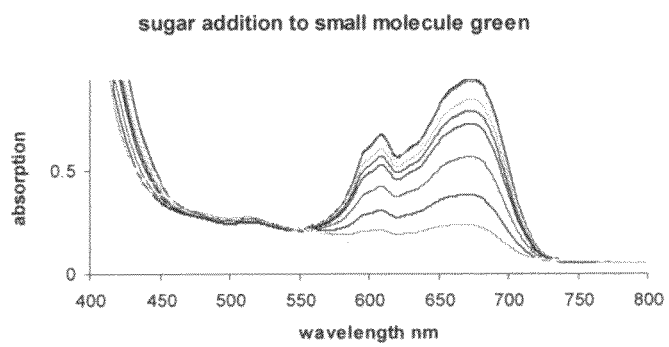
FIGS. 15A-B. Decreasing absorbance at 671 nm upon addition of sugar solutions to A) small molecule terpy-$Co^{2+}$ complex and B) polymer-$Co^{2+}$ complex.
Figure 15B:
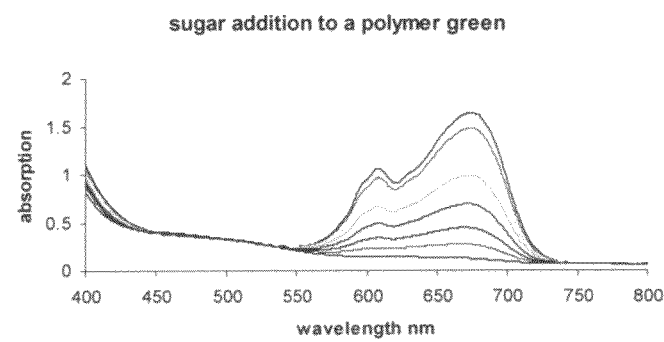

With reference to FIGS. 15A-B, small molecule-and polymer-complexes with Co$^{2+}$ undergo colorimetric change upon contact with an aqueous sugar solution.

Example 12c

The colorimetric change of the preceding example (from green to brown) was observed upon contact with a paper strip coated with a Co$^{2+}$ complex of this invention.

Example 12d

Figure 16A:
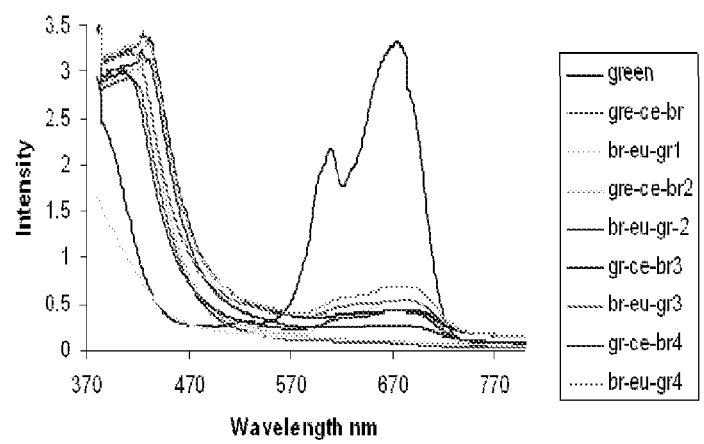
FIGS. 16A-B. A) Absorption spectra and B) response at 671 nm of green and brown solutions for the demonstration of "on-off" behavior.
Figure 16B:
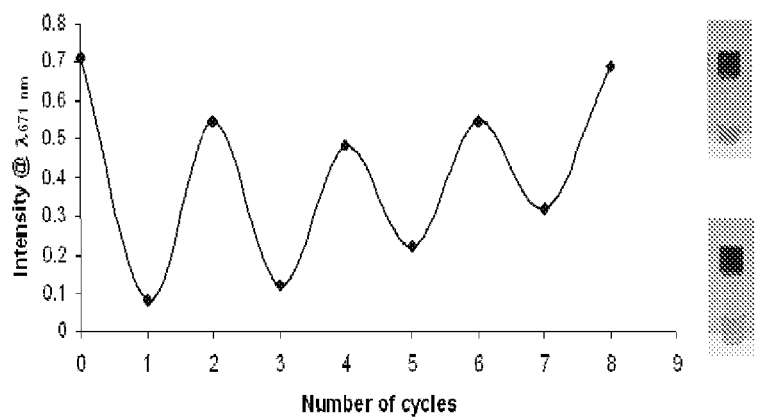

With reference to FIGS. 16A-B, the "on-off" capacity available through the Co$^{2+}$/Co$^{3+}$ redox chemistry used in conjunction with this invention, was demonstrated with alternate exposures of such a complex (Co$^{2+}$) to a hydroxy compound and then exposure (Co$^{3+}$) to a chlorohydrocarbon.

The invention claimed is:
1. A method of detecting Hg$^{2+}$ ion, the method comprising:
   contacting a compound comprising a terpyridine moiety with a sample to be tested for the presence of Hg$^{2+}$ under a condition such that, if $Hg^{2+}$ ions are present in the sample, at least some of $Hg^{2+}$ ions present will bind with the terpyridine moiety; and detecting a colorimetric change of the sample resulting from the binding of $Hg^{2+}$ ions, if present, with the terpyridine moiety, wherein the compound is a polymer and the terpyridine moiety is pendent to a monomeric component of the polymer, and wherein the colorimetric change is detectable in the presence of one or more ions selected from the group consisting of $Ag^+$, $Ba^{2+}$, $Pb^{2+}$, $Cd^{2+}$, $Ca^{2+}$, $Mg^{2+}$, and $Zn^{2+}$ and provides a limit of detection of 2 ppb $Hg^{2+}$ at 557 nm, wherein the polymer comprises a backbone selected from the group consisting of a poly(alkylene oxide) backbone, a poly(alkylene) backbone and a poly(methylmethacrylate) backbone.

2. The method of claim 1, wherein the sample comprises at least one non-Hg ion.

3. The method of claim 2, wherein the colorimetric change comprises a visible color change.

4. The method of claim 2, wherein the polymer comprises the poly(alkylene oxide) backbone.

5. The method of claim 2, wherein the polymer comprises the poly(alkylene) backbone.

6. The method of claim 2, wherein the polymer comprises the poly(methylmethacrylate) backbone.

7. The method of claim 2, wherein the polymer is in a medium selected from solid and liquid media.

8. The method of claim 7, wherein the solid medium comprises a substrate coupled to the polymer compound, the substrate being selected from metallic, polymeric and cellulosic substrates.

9. The method of claim 8, wherein the solid medium comprises a paper strip coated with the compound.

* * * * *